(12) United States Patent
Maack

(10) Patent No.: US 7,182,965 B2
(45) Date of Patent: Feb. 27, 2007

(54) SOLUBLE COMPOSITION CONTAINING SPOROPOLLENIN AND THE USE THEREOF

(75) Inventor: Andreas Maack, Schipperkamp 29, D-31717 Nordsehl (DE)

(73) Assignee: Andreas Maack, Nordsehl (DE)

( * ) Notice: Subject to any disclaimer, the term of this patent is extended or adjusted under 35 U.S.C. 154(b) by 0 days.

(21) Appl. No.: 10/514,806

(22) PCT Filed: Apr. 19, 2003

(86) PCT No.: PCT/EP03/04111

§ 371 (c)(1),
(2), (4) Date: Nov. 12, 2004

(87) PCT Pub. No.: WO03/094942

PCT Pub. Date: Nov. 20, 2003

(65) Prior Publication Data

US 2005/0191374 A1    Sep. 1, 2005

(30) Foreign Application Priority Data

May 13, 2002   (DE) ............................... 102 21 212

(51) Int. Cl.
*A61N 65/00* (2006.01)
*A61K 9/00* (2006.01)
*A61K 47/00* (2006.01)

(52) U.S. Cl. ..................... 424/778; 424/725; 424/400; 424/439

(58) Field of Classification Search ................ 424/778, 424/725, 400, 439
See application file for complete search history.

(56) References Cited

U.S. PATENT DOCUMENTS

| 5,925,684 A | 7/1999 | Schweikert et al. |
| 2004/0185063 A1 | 9/2004 | Ray |

FOREIGN PATENT DOCUMENTS

| DE | 196 09 476 | 9/1997 |
| DE | 199 02 724 | 7/2000 |

OTHER PUBLICATIONS

M. Arslan et al; Frensenlus Environmental Bulletin; vol. 13; No. 7.2004; pp. 616-619; Removal of Cadmium (II) . . . .
E. Pehlivan et al; Jour. Of Colloid & Interface Sc. 170, 320-325 (1995); The effect of pH & temperature on the sorption . . . .
Pollen Sporopollenin Degradation . . . by E. Dominguez et al. Sex Plant Report Dec. 1999.
Carotenoids by Eisier et al. (Burghauser Verlag Basel und Stuttgart 1971).

*Primary Examiner*—Susan Hoffman
*Assistant Examiner*—Randall Winston
(74) *Attorney, Agent, or Firm*—Andrew Wilford; Jonathan Myers

(57) ABSTRACT

A composition containing sporopollenin is disclosed which is characterized in that it is present as a solution and, aside from 0.01% to 12% by weight, preferably 0.1% to 5% by weight, of sporopollenin, it also contains 0.01% to 17% by weight, preferably 0.1% to 10% by weight, of at least one emulsifier, it also contains 71.00% to 99.98% by weight, preferably 85% to 99.80% by weight, of at least one hydrophilic solvent, and the use of this composition for cosmetic, pharmaceutical purposes, as chelating agents and nutritional supplements is also disclosed.

20 Claims, No Drawings

SOLUBLE COMPOSITION CONTAINING SPOROPOLLENIN AND THE USE THEREOF

CROSS REFERENCE TO RELATED APPLICATIONS

This application is the US national stage of PCT Application PCT/EP03/04111 filed on 19 Apr. 2003, based on German national application 102 21 212.0 filed on 13 May 2002.

The present invention relates to a composition containing sporopollenin and to its use, as elaborated upon below.

The term sporopollenin refers to the following according to, for example, Römpp—Lexikon Naturstoffe [Römpp Encyclopedia Natural Products], 1997, page 604 under the entry "sporopollenin": "polyterpenes found in pollen which are possibly formed as a result of oxidative polymerization from carotinoids and their esters".

As a polyterpene, however, this compound does not have anything in common with the corresponding carotene monomers such as, for instance, beta-carotene.

Sporopollenin is also found in very small amounts in the spores and pollen of plants such as, for example, ferns, club moss, flowers, in addition to which it is also a component of special types of algae. The production of sporopollenin in the form of microcapsules is described in German Preliminary Published Application No. 199 02 724 and so is its use as a mechanical support phase for the encapsulation of substances and cells, although the sporopollenin is present in the capsules as a dispersion and not as a solution.

R. Wiermann, $^1$H-NMR-Analysis of Sporopollenin from *Typha Angustifolia* in Phytochemistry, Volume 50 (1999), pages 1095–1098, reports in the analytical section about the insolubility of sporopollenin, which can only be produced in very small quantities. The authors report that they only managed to dissolve sporopollenin in amounts of 5 mg per 5 ml in highly polar solvents such as aminoethanol.

The present invention has the objective of preparing a composition containing sporopollenin which can be dissolved either alone or in combination with biologically active ingredients.

This objective is achieved in that sporopollenin is brought into contact with a specific quantity of at least one emulsifier and with a specific quantity of at least one hydrophilic solvent, thus dissolving it in a known manner by means of heating to a temperature above room temperature, that is to say, 10° C. to 25° C. [50° F. to 77° F.].

Thus, the present invention firstly refers to a composition containing sporopollenin which is characterized in that it is present in the form of a solution and, aside from 0.01% to 12% by weight, preferably 0.1% to 5% by weight, of sporopollenin, it also contains 0.01% to 17% by weight, preferably 0.1% to 10% by weight, of at least one emulsifier and 71.00% to 99.98% by weight, preferably 85% to 99.80%, of at least one hydrophilic solvent.

The term solution as employed in the present invention refers to a transparent liquid which, depending on the concentration, ranges from being more or less light-colored to slightly yellow and has a somewhat high viscosity which results primarily from the viscosity of the solvent itself.

According to a preferred embodiment of the present invention, this composition comprises a hydrolyzable ether compound as the emulsifier, a hydrolyzable glycoside, a hydrolyzable carboxylic acid anhydride or a hydrolyzable carboxylic acid amide.

If the hydrolyzable compound is an ester compound, this can be either an emulsifier with one alcohol component or an emulsifier with several different alcohol components.

If the preferred embodiment of the emulsifier is an emulsifier with one alcohol component, this alcohol can be monovalent or polyvalent and can optionally contain additional functional groups.

Examples of emulsifiers with a monovalent alcohol component are those monovalent alcohols derived from fatty alcohols such as, for instance, those derived from 2-ethyl hexanol, from dodecanol, from octadecanol. Examples worth mentioning here are dioctyl-sulfosuccinic acid diester (Na-salt), the sodium salt of lauryl sulfuric acid, the sodium salt of stearyl fumaric acid, stearyl tartrate and stearyl citrate.

Other examples of hydrolyzable ester compounds are emulsifiers with a bivalent alcohol component or its condensates, for instance, on the basis of glycol, polyglycol, 1,2-propane diol, poly-1,2-propane diol, 1,3-butane diol as well as glycol-1,2-propane diol mixed condensates. Examples of these are glycol monoesters and glycol diesters, polyoxyethylene fatty acid esters, of the type sold under the brand name "MYRJ" and as propylene glycol fatty acid esters.

Other examples of hydrolyzable ester compounds of trivalent alcohols and their condensates are those on the basis of glycerin, be it from cooking fatty acids as the sole acid component, that is to say, fatty acid monoglycerides or fatty acid diglycerides, modified fatty acids alone or with cooking fatty acids, soy fatty acids, which are thermally oxidized, or other acids as the acid component in addition to fatty acids, such as phosphoric acid, phosphatide acids, lecithins, acetic acid, lactic acid, succinic acid, tartaric acid, O,O-diacetyl tartaric acid, citric acid, sulfoacetic acid. Such products are sold under the designations emulsifier yn, Emphos (Na-salt), soy lecithin, egg lecithin, fractionated lecithin, aceto(mono)glycerides, acetylated monoglycerides or diglycerides, monoglyceride acetate, lactoglycerides, lactylated monoglycerides or diglycerides, monoglyceride lactate, succinoglycerides, succinylated monoglycerides, tartaric acid glycerides, monoglyceride tartrate, monoglyceride diacetyl tartrate, citroglycerides, citric acid (mono)glyceride esters as well as ethoxylated monoglycerides and diglycerides, for instance, under the designation "polyglycerate".

Additional examples of trivalent alcohols and their condensates are derivatives of polyglycerin, be it cooking fatty acids as the sole carboxylic acid component in the form of polyglycerin fatty acid esters, modified fatty acids such as polyglycerin polyricinoleate, polyglycerin ester of dimerized soy oil fatty acids as well as other acids as the acid component in addition to fatty acids such as, for instance; tartaric acid polyglycerides.

Other examples of hydrolyzable esters with alcohol components are tetravalent alcohols such as, for instance, pentaerythritol, pentavalent alcohols, hexavalent alcohols such as sorbitol, monoglycerides and di-anhydrides like sorbitan fatty acid ester, which are sold under the designations "Span", also polyoxyethylene sorbitans such as polyoxyethylene sorbitan fatty acid esters, which are sold under the designations "polysorbate" or "Tween".

Other examples of hydrolyzable ester compounds are those with a carbohydrate as the alcohol component, be it saccharose or a saccharose fatty acid ester.

Additional examples of hydrolyzable ester compounds are hydroxy carboxylic acids as the alcohol component, be it lactic acid and its condensates, such as lactyl fatty acid esters or stearoyl-2-lactyl lactic acid and finally polyol glycosides as the alcohol component in the form of 1,2-propane diol glycoside fatty acid esters and glycerin glycoside fatty acid esters.

Finally, the hydrolyzable ester group can also have several different alcohol components, whereby the different alcohol component in the same reaction mixture can be a single alcohol component in the same ester molecule such as, for example, fatty acids as the carboxylic acid component such as polyglycol-/glycerin esters of fatty acids, 1,2-propane diol-/glycerin esters of fatty acids, sorbitan-/glycerin esters of fatty acids, polyoxyethylene-sorbitan-/glycerin esters of fatty acids, saccharose-/glycerin esters of fatty acids, although, aside from the fatty acid, they can also contain another carboxylic acid component such as, for instance, 1,2-propane diol-/glycerin mixed esters of fatty acids and lactic acid.

Instead of one hydrolyzable ester group, it is, of course, also possible to use hydrolyzable ester groups. Examples of these are polyglycol fatty alcohol ethers of the type sold under the designation "Brij", such as polyoxyethylene lauryl ether Brij 35.

Instead of a hydrolyzable ether group, it is also possible to use a hydrolyzable glycoside group with the corresponding saponins or glycosides of hydroxy fatty acid emulsifiers.

Examples of hydrolyzable carboxylic acid anhydride emulsifiers are sorboyl palmitate or hydrolyzable carboxylic acid amides on the basis of bile acid amides and fatty acid monoalkanol amides and dialkanol amides.

According to another preferred embodiment, the emulsifier is a hydrophilic non-ionic emulsifier which alternatively can also be defined by the HLB value (HLB=hydrophilic-lipophilic balance) of an emulsifier. This has to do with the relative strength of the polar groups and of the apolar radical and the resultant affinity of the emulsifier to water. It has been surprisingly found that, according to the invention, non-ionic emulsifiers having an HLB value ranging from 8 to 18, but especially from 10 to 17, can be employed.

As another component, a hydrophilic solvent is employed which is water or a hydrophilic organic solvent. This can be, for instance, an alkanol having 1 to 22 carbon atoms. It can also be a monovalent alcohol, whereby preference is given to ethanol, n-propanol and iso-propanol.

Moreover, this can also be a polyvalent alcohol, in other words, an alcohol containing at least two alcoholic hydroxyl groups in the molecule. Examples of this are diols, glycols, glycerin as well as sugar alcohols, polyalkylene glycols such as polyethylene glycol, polyether polyols and polyester polyols.

Moreover, this can also be an ester having 2 to 33 carbon atoms, whereby the corresponding esters derived from carboxylic acids having 1 to 8 carbon atoms are preferred.

Another subject matter of the present invention is the preparation of a composition containing sporopollenin, whereby the sporopollenin is employed here as a solid substance and it is used either directly or else in combination with appropriate cosmetic and pharmaceutical active ingredients. In particular, it has been found to be advantageous to utilize this solid substance containing sporopollenin either alone or else together with other active ingredients for the treatment of microbial, especially bacterial, diseases, for the treatment of poisoning as well as for the cosmetic treatment of the skin, particularly facial skin, against age-related and/or sun-related wrinkle formation. As an alternative, it is also possible to administer the solid substance containing sporopollenin as a nutrient or food product to vertebrates, especially to mammals, including humans.

Another subject matter of the present invention is the preparation of biological compositions that contain the above-mentioned sporopollenin solutions together with commonly employed auxiliaries and additives.

These are, for instance, appropriate cosmetic compositions that contain such a sporopollenin solution in the form of an oil, an ointment, a cream, a gel embedded in liposomes or else as a solid stick.

According to another preferred embodiment, the composition can be present in the form of a hydrophilic ointment. When it is to be used as a surface ointment, it is an option to employ macrogels, that is to say, polyethylene glycol or polyoxyethylene polymers as the ointment base in the case of hydrophilic ointments. In this context, we would like to refer, for instance, to the monograph titled "Arzneimittelformlehre" [Drug forms] by Schöffling, Stuttgart, Germany, 1998, pages 310 to 319 as well as pages 328 to 337 and to the substances as well as production methods described therein, and also to Bauer, Pharmazeutische Technologie [Pharmaceutical technology], Stuttgart, Germany, 1986, pages 312 to 323 as well as pages 330 to 331.

According to another preferred embodiment, the composition can be present in the form of a hydrophilic oil-in-water (O/W) cream. We again would like to refer, for instance, to the monograph by Schöffling, pages 320 to 324 and to Bauer, pages 323 to 328 as well as pages 331 to 332.

In another preferred embodiment, the composition can be present as a gel. Hydrophilic gels include hydrogels on the basis of polyacrylates and acrylic acids as well as on the basis of cellulose ethers. In this context, we would like to refer, for instance, to the above-mentioned monograph by Schöffling, pages 324 to 327 as well as to Bauer, pages 329 to 330.

According to another preferred embodiment, the composition can be present as an oil on the basis of at least one fatty acid ester of a mineral or fatty oil. Such substrates are normally designated as skin oils. We refer, for example, to the overview by G. A. Novak titled "Die kosmetischen Präparate" [Cosmetic preparations], $2^{nd}$ edition, page 657 ff.

As is known to the person skilled in this field, all of the above-mentioned pharmaceutical or cosmetic galenic forms of administration can be obtained in a familiar manner from the corresponding aqueous and/or fatty phases by being mixed and, if applicable, homogenized with the sporopollenin solutions.

According to another preferred embodiment, the compositions according to the invention also encompass pharmaceutical compositions containing the above-mentioned sporopollenin solution in the form of an oil, a cream or, if applicable, a capsule.

Regarding the galenic forms of oil and cream, we would like to make reference to the above-mentioned literature sources by Schöffling and Bauer. Moreover, pharmaceutical compositions can also be employed in capsule form. If the sporopollenin solutions according to the invention are to be used in such a case, especially the appropriate soft gelatin capsules should be used. In this context, we make reference to the appropriate literature on galenics by Schöffling on pages 164 to 179.

Alternatively, the compositions containing sporopollenin can also be employed in a solid form, for instance, through administration in hard gelatin capsules. In this regard, we make reference to the appropriate galenics on this in Schöffling, pages 168 to 178.

Consequently, another subject matter of the present invention is the use of solutions containing sporopollenin of the above-mentioned type for the treatment of microbial, especially bacterial, diseases for topical, oral and parenteral administration in humans and animals.

According to another preferred embodiment, the solutions containing sporopollenin of the above-mentioned type can be employed for the cosmetic treatment of the skin, especially facial skin, against age-related and/or sun-related wrinkle formation. Sporopollenin can also be used as a solution or as a solid substance for the treatment of poisoning.

According to another preferred embodiment, the above-mentioned solution containing sporopollenin can be employed as a chelating agent, especially as a component of ion exchangers or in wastewater purification. Here, it was found according to the embodiment that sporopollenin is able to remove, for instance, heavy metal ions from aqueous solutions at a rate of more than 60%, at times over 99%, already after an exposure time of just a few hours.

According to another preferred embodiment, the above-mentioned solutions containing sporopollenin can be employed as nutritional supplements for vertebrates, especially for mammals, pets and domestic animals as well as for humans.

For this purpose, according to a special embodiment, the sporopollenin thus used can be employed not only as a solution but also as a solid substance.

Moreover, sporopollenin in solution or as a solid substance can be used as an ingredient in beverages to which, if applicable, conventional auxiliaries or additives have been added.

The present invention will be explained in greater detail below by means of preparation examples and embodiments. The ratios given in this context always refer to weight ratios.

PREPARATION EXAMPLE 1

By reacting 87.9 g of glycerin, anhydrous, Ph. Eur., with 12.0 g of the emulsifier polyoxyethylene sorbitan monooleate (E 433) and 0.1 g of sporopollenin (catalog no. 16867, made by Polysciences Europe GmbH, Eppelheim, Germany or available from RTC GmbH, Nordsehl, Germany) under vigorous agitation and heating to a temperature between 40° C. and 50° C. [104° F. and 122° F.] for a period of about 30 minutes, a sporopollenin solution is prepared which remained in solution after cooling off to room temperature. This mixture did not exhibit any de-mixing of the components even after six weeks.

PREPARATION EXAMPLE 2

Example 1 was repeated, except that 91.6 g of propylene glycol, Ph. Eur., were used as the solvent, 7.9 g of polyoxyethylene sorbitan monooleate (E 433) were used as the emulsifier and 0.5 g of sporopollenin was used. After the cooling off, a correspondingly slightly yellow colored solution was obtained which de-mixed after two weeks.

PREPARATION EXAMPLE 3

Example 1 was repeated, except that 91.9 g of water were used as the solvent, 8.0 g of Brij 35 P polyoxyethylene lauryl ether (Laureth-23) were added as the emulsifier and 0.1 g of sporopollenin was used. After a cooling off period, a correspondingly slightly yellow colored solution was obtained which did not show any signs of de-mixing even after six weeks.

PREPARATION EXAMPLE 4

By means of agitation, heating to about 40° C. [104° F.] and subsequent cooling, a mixture of 0.1 g of sporopollenin was obtained with a mixture of 88.0 g of 90%-ethanol and 11.9 g of the emulsifier Myrj 45 (polyoxyethylene-8-stearate). The solution did not show any signs of de-mixing even after six weeks.

PREPARATION EXAMPLE 5

By means of agitation and heating, a solution was obtained from 5 mg of sporopollenin corresponding to 0.12% by weight, from 483 mg of the emulsifier polyoxyethylene sorbitan monooleate (E 433)=11.77% by weight as well as from 3617 mg of Miglyol 812 neutral oil (mixture-acidic triglyceride of the fractionated coconut oil fatty acids $C_8$–$C_{10}$; available from Degussa AG, Troisdorf plant, Germany)=88.11% by weight; this solution did not de-mix for at least two days.

PREPARATION EXAMPLE 6

By means of agitation and heating, a solution was obtained from 4 mg of sporopollenin corresponding to 0.48% by weight, from 146 mg of the emulsifier polyoxyethylene sorbitan monooleate (E 433)=17.40% by weight as well as from 689 mg of distilled water=82.12% by weight; this solution exhibited partial de-mixing after two days in the form of sporopollenin residues on the bottom which, however, dissolved once again when the heating and stirring procedures were repeated.

PREPARATION EXAMPLE 7

By means of agitation and heating, a solution was obtained from 4 mg of sporopollenin corresponding to 1.29% by weight, from 43 mg of the emulsifier polyoxyethylene sorbitan monooleate (E 433)=13.87% by weight as well as from 263 mg of 70%-iso-propanol=84.84% by weight; this solution exhibited partial de-mixing after about two days but it dissolved once again when the heating and stirring procedures were repeated.

PREPARATION EXAMPLE 8

By means of agitation and heating, a solution was obtained from 8 mg of sporopollenin corresponding to 0.62% by weight, from 137 mg of the emulsifier polyoxyethylene sorbitan monooleate (E 433)=10.54% by weight as well as from 1155 mg of glycerin DAB=88.84% by weight; this solution exhibited partial de-mixing after three days since all of the sporopollenin had dispersed in the emulsifier.

PREPARATION EXAMPLE 9

By means of agitation and heating, a solution was obtained from 6 mg of sporopollenin corresponding to 0.62% by weight, from 66 mg of the emulsifier polyoxyethylene sorbitan monooleate (E 433)=10.54% by weight as well as from 394 mg of propylene glycol DAB=88.64% by weight; this solution exhibited partial de-mixing after about three days since some of the sporopollenin was dispersed in the emulsifier but a sediment of undissolved sporopollenin had formed.

PREPARATION EXAMPLE 10

By means of agitation and heating, a solution was obtained from 3 mg of sporopollenin corresponding to 0.74% by weight, from 46 mg of the emulsifier Brij 35 P (Laureth-23)=11.30% by weight as well as from 358 mg of 90%-ethanol; this solution exhibited partial de-mixing after about two days although the sporopollenin residues on the bottom could be dissolved once again when the heating and stirring procedures were repeated.

PREPARATION EXAMPLE 11

By means of agitation and heating, a solution was obtained from 7 mg of sporopollenin corresponding to 1.08% by weight, from 46 mg of the emulsifier Brij 35 P (Laureth-23)=7.11% by weight as well as from 594 mg of 70%-iso-propanol=91.81% by weight; this solution exhibited partial de-mixing after about two days although the sporopollenin residues on the bottom could be dissolved once again when the heating and stirring procedures were repeated.

PREPARATION EXAMPLE 12

By means of agitation and heating, a solution was obtained from 3 mg of sporopollenin corresponding to 0.34% by weight, from 78 mg of the emulsifier Brij 35 P (Laureth-23)=8.99% by weight as well as from 787 mg of distilled water=91.81% by weight; this solution exhibited partial de-mixing after about two days although the sporopollenin residues on the bottom could be dissolved once again when the heating and stirring procedures were repeated.

PREPARATION EXAMPLE 13

By means of agitation and heating, a stringy, viscous solution was obtained from 3 mg of sporopollenin corresponding to 0.63% by weight, from 77 mg of the emulsifier Brij 35 P (Laureth-23)=16.04% by weight as well as from 400 mg of propylene glycol=83.33% by weight.

PREPARATION EXAMPLE 14

By means of agitation and heating, a solution was obtained from 3 mg of sporopollenin corresponding to 0.61% by weight, from 68 mg of the emulsifier Myrj 45 (polyoxyethylene-8-stearate)=13.85% by weight as well as from 420 mg of 90%-ethanol=85.54% by weight.

PREPARATION EXAMPLE 15

By means of agitation and heating, a solution was obtained from 5 mg of sporopollenin corresponding to 0.38% by weight, from 180 mg of the emulsifier Myrj 45 (polyoxyethylene-8-stearate)=13.49% by weight as well as from 1149 mg of distilled water=86.13% by weight.

PREPARATION EXAMPLE 16

By means of agitation and heating, a yellowish, viscous solution was obtained from 9 mg of sporopollenin corresponding to 0.65% by weight, from 65 mg of the emulsifier Myrj 45 (polyoxyethylene-8-stearate)=4.67% by weight as well as from 1318 mg of distilled water=94.68% by weight.

PREPARATION EXAMPLE 17

By means of agitation and heating, a yellowish, viscous solution was obtained from 2 mg of sporopollenin corresponding to 0.58% by weight, from 20 mg of the emulsifier Myrj 45 (polyoxyethylene-8-stearate)=5.80% by weight as well as from 323 mg of propylene glycol=93.62% by weight.

GALENIC EXAMPLE 1

Oil

By mixing 5 g of the sporopollenin solution according to the invention as described in Preparation Example 1 with 75 g of Miglyol 812 neutral oil and 20 g of paraffin oil, an oil was prepared that can be administered topically both for cosmetic and pharmaceutical purposes. If desired, a scent or perfume can be added, in which case the fraction of paraffin oil is correspondingly reduced.

GALENIC EXAMPLE 2

Cream with Sporopollenin Solution 6 g of sporopollenin solution (composition: 92.25% glycerin, anhydrous, Ph. Eur., 7.60% polyoxyethylene sorbitan monooleate, 0.15% sporopollenin) and 493 g of DAC base cream (for the composition, see Schöffling op. cit., page 321). The solution, which was at a temperature of approximately 50° C. [122° F.], is admixed with the DAB base cream while being stirred. After the solution has cooled down to room temperature under agitation, it is evaporated until the desired consistency is achieved, after which it is homogenized once again. The result is a pale yellowish cream.

GALENIC EXAMPLE 3

Cream with Solid Sporopollenin

Sporopollenin and Lipoid SLM 2005 Base 2 mg of sporopollenin solution corresponding to 0.56% by weight, 211 mg of 90%-ethanol=58.61% by weight as well as 147 mg of Lipoid SLM 2005 (skin care cream on the basis of lecithin/glycerin, a product manufactured by Lipod GmbH of Ludwigshafen, Germany)=40.83% by weight.

Sporopollenin is suspended at a temperature of 50° C. [122° F.] in ethanol, then this suspension is admixed with Lipoid SLM 2005 under agitation. After the solution has cooled down to room temperature under agitation, it is evaporated until the desired consistency is achieved. The result is a pale yellowish cream (170 mg, concentration of sporopollenin of 1.18%) that smells like ethanol. Optionally, thickeners (for instance, xanthan) can be incorporated for purposes of influencing the viscosity.

GALENIC EXAMPLE 4

Cream

Sporopollenin and DAC Base Cream 5 mg of sporopollenin solution corresponding to 0.61% by weight, 417 mg of 90%-ethanol=50.73% by weight and 400 mg of DAC base cream=48.66% by weight.

Sporopollenin is suspended at a temperature of 50° C. [122° F.] in ethanol, then this suspension is added to the DAC base cream under agitation. After the solution has cooled down to room temperature under agitation, it is evaporated until the desired consistency is achieved, after which it is homogenized once again. The result is a pale yellowish cream that still smells faintly like ethanol.

APPLICATION EXAMPLE 1

A sporopollenin solution made according to Preparation Example 1 was tested in terms of its compatibility with the skin. In this procedure, the GLP Guidelines and the recommendations of the COLIPA work group (Walker A. P. et al.: Test Guidelines for Assessment of Skin Compatibility of Cosmetic Finished Products in Man, Food and Chemical Toxicology 34, 1996, pages 651 to 660) were observed.

The trial involved 50 test subjects, that is to say, 21 persons with healthy skin, 11 atopic persons, 2 allergic persons and 16 persons with a sensitive skin, ranging in age from 18 to 65 years of age.

The product according to Preparation Example 1 was applied in undiluted form onto the backs of the test subjects by means of square plastic chambers for 48 hours under occlusion. The model noxious substance sodium lauryl sulfate at a concentration of 1% in water served as the positive control. Water itself served as the negative control.

The evaluation of the test reaction was carried out after 48 and 72 hours in accordance with the modified Draize test. The test findings show that, under the test conditions, the 1%-solution of SDS yielded a positive reaction in 14 test subjects. As expected, the negative control showed no reaction in any of the persons. On the basis of the test results and of the selected test conditions, the solution according to the invention can be classified as safe in terms of a possible skin irritating effect.

APPLICATION EXAMPLE 2

Determination of the wrinkle depth in the face by means of the optical 3D in-vivo skin measuring system method called "PRIMOS".

Measurement of the Wrinkle Depth

The determination is made employing the "PRIMOS" (Phaseshift-Rapid In-vivo Measurement Of Skin) 3D in-vivo skin measuring system—manufactured by the company GM Meßtechnik GmbH of 14513 Teltow/Berlin, Germany). This optical 3D in-vivo skin measuring system is based on the so-called stripe projection technique. In the stripe projection technique, a projection lens is used to project a parallel stripe pattern onto the skin surface and then imaged by means of an imaging lens onto the chip of a CCD matrix camera. Minute differences in the skin height cause the parallel stripes to be deflected. The magnitude of the deflection constitutes both a qualitative as well as a quantitative measure of the appertaining height profile. By means of the fixed reference angle between the projection lens and the camera system, the profile heights can be determined on the basis of simple triangulation equations. The possible profile height resolution is determined on the basis of the used effective wavelength $\lambda_{\mathit{eff}}$ by the height difference to be measured.

The parameter $R_{max}$ (German standard DIN 4768/1) is selected in order to describe the wrinkle depth. $R_{max}$ is the maximum raw depth, that is to say, the distance between the line of the elevation and the line of the depression within the measured segment.

Execution of the Test

The female test subjects were informed about the scope and significance of the trial. Subsequently, they signed an informed consent form. They were selected according to the following criteria:

Inclusion Criteria:
women older than 18 years of age
clinically healthy
clearly visible wrinkles in the area of the eyes Exclusion Criteria:
skin diseases
pregnancy All of the test subjects could drop out of the study at any time without the need to provide any reasons. Each trial participant received a detailed set of instructions about the application.

The test subjects were instructed not to apply any external products to the face starting three days prior to the beginning of the trial as well as during the entire duration of the trial.

During use of the product, only water or a mild syndet soap (Eubos® liquid-blue; manufactured by Dr. Holbein of D-53340 Meckenheim-Merl, Germany) could be used for cleaning the test fields.

The measurements were conducted before the first application at precisely defined places on the face (eye area: crow's feet). Additional measurements were performed after one and two weeks of use of the product 8 to 12 hours after the daily application (acclimatization time: 30 minutes, room temperature: 20° C.±1° C. [68° F.±1.8° F.], relative humidity: 50%±10%). The product was used once per day by the test subjects (on the face in the evening) so as to duplicate as closely as possible the mode of use by consumers of the test product. The left half of the face was treated with the test product while the right half remained untreated and served as the control.

Biometrics

The measured data was entered into the computer centrally after a thorough plausibility check and quality assurance. The data was evaluated by means of the software WinSTAT® Add-in for Excel—R. K. Fitch, Germany. The Wilcoxon matched pairs signed rank test was selected for the statistical analysis. $p<0.05$ was considered as indication of a statistically significant difference.

Findings

Reduction of the Wrinkle Depth

After 14 days of regular use of the test product on the face (eye wrinkles), a statistically significant reduction ($p<0.05$) of the wrinkle depth was found in comparison to the control. The average reduction in the depth of the wrinkles was the following (figures in %, relative to the initial value):

|  | Product | Untreated |
|---|---|---|
| Day 7 | 4.7 | −1.3 |
| Day 14 | 8.9*) | −1.5 |

*) $p < 0.05$ versus untreated

Toxicity

The oral toxicity of the compositions containing sporopollenin according to the invention, in the example of the algae extract Caelico® (sold by RTC GmbH of Nordsehl, Germany) containing sporopollenin, suspended in a 0.8%-aqueous hydroxypropyl methyl cellulose gel was tested in CD® rats and this was done according to OECD Guideline 423 and EC Guideline L 248: B1 tris (ATC method) (corresponding U.S. Food and Drug Administration Good Laboratory Practice Regulations 21 Code of Federal Regulations, Part 58, corresponding to the Japanese Guidelines for Non-Clinical Studies of Drugs, Manual 1995, Guidelines for Toxicity Studies of Drugs, Japanese Ministry of Health and Welfare) in which the placebo level as well as the $LD_{50}$ level were at more than 2 grams per kilogram of body weight in the case of oral intake.

GALENIC EXAMPLE 5

Animal Feed with Solid Sporopollenin 0.1 g of sporopollenin according to Preparation Example 1 and 9.9 g (or 4.95 g) of a suitable carrier material (lactose or corn starch) are mixed together in a mortar and triturated until a homogenous mixture has been obtained. The content of sporopollenin is 1% (or 2%, respectively).

EXAMPLE 6

Beverage with Dissolved Sporopollenin

| Ingredients | Quantity in grams |
|---|---|
| water | 920 |
| glucose syrup DE 70 | 90 |
| orange juice concentrate 65° Bx | 4.15 |
| citric acid (anhydrous) | 3.5 |
| sporopollenin according to Preparation Example 1 | 2 |
| modified starch | 1.37 |
| grapefruit juice concentrate 60° Bx | 1.25 |
| sunflower oil | 1.1 |
| lemon juice concentrate 65° Bx | 0.55 |
| carboxymethyl cellulose | 0.74 |
| beta-carotene | 0.5 |
| sodium benzoate 20% $H_2O$ | 0.5 |
| vitamin C | 0.5 |
| xanthan | 0.46 |
| potassium sorbate | 0.1 |
| acesulfam K | 0.1 |
| aspartam | 0.1 |
| Sum | 1 liter |

The beverage is made by weighing in water, glucose syrup, sodium benzoate, then the juice concentrates and the oil, followed by the weighing in and mixing of the pulverulent components, except for the beta-carotene. This powder mixture is admixed with the liquid phase under agitation at approximately 5000 rpm, then homogenized 5 times at 220 bar, the beta-carotene is added to the beverage, the mixture is pasteurized at 90° C. [194° F.] for 10 minutes and finally stored at +4° C. [+39.2° F.].

The contents of the fruit juice concentrates, citric acid and beta-carotene can be varied as a function of the envisaged flavor. The content of sporopollenin can likewise be varied.

The sweeteners and beta-carotene are not absolutely necessary, in which case correspondingly more glucose syrup should be used.

Heavy Metal Bonding or Removal

The MS measurements below were made using a SPECTROFLAME—ICP P spectrometer of type FLAMEFV04-38/043, S/N: 0213/90, voltage: 220 V/50 Hz. Output: 5500 VA made by SPECTROANALYTICAL INSTRUMENTS GmbH of Kleve, Germany.

APPLICATION EXAMPLE 3

15 mg of sporopollenin according to Preparation Example 1 (Experiment 1) are added to a solution consisting of 11 mg of lead acetate trihydrate (Merck, No. 10732), 11 mg of cadmium nitrate-4-hydrate (Riedel de Haen, No. 11714), 11 mg of arsenic(V) oxide hydrate (Fluka, No. 11304) and 30 ml of distilled water. The solution is stirred for 2 hours and the sporopollenin is filtered off. Then 1 ml of this filtered solution is employed in the atom absorption spectrometer measurement. Prior to the measurement, the solution is diluted with distilled water at to a ratio of 1:20.

APPLICATION EXAMPLE 4

15 mg of sporopollenin according to Preparation Example 1 (Experiment 2) are added to a solution consisting of 11 mg of lead acetate trihydrate, 11 mg of cadmium nitrate-4-hydrate, 11 mg of arsenic(V) oxide hydrate and 30 ml of distilled water. The solution is stirred for 2 hours and the sporopollenin is filtered off. Then 1 ml of this filtered solution is employed in the atom absorption spectrometer measurement. Prior to the measurement, the solution is diluted with distilled water at a ratio of 1:20.

Measuring Method

The samples were diluted—see the experiment description—and the measurement was carried out simultaneously employing ICP-OES (Inductively Coupled Plasma—Optical Emission Spectrometry). Optical emission spectrometry with inductively coupled plasma (ICP-OES) was employed for the analysis of trace elements in solutions within the concentration range from mg/l to µg/l. Fundamentally, this method allows the simultaneous determination of all metals and a few non-metals (up to 60 elements) from acidified, aqueous solutions up to a total content of the dissolved substance of approximately 10 g/l. With ICP-OES, a liquid sample is atomized and the atoms are excited to emit light by means of an inductively coupled plasma (temperature of up to 10,000 K). The emitted light is dispersed with a grating. An electron multiplier that serves as a detector transforms light into electric signals. Simultaneously measuring spectrometers are capable of detecting many emission lines at the same point in time.

| | Measured results | | | | | |
|---|---|---|---|---|---|---|
| | Content: 97.00% As (193,6956 nm) | | Content: 99.00% Cd (226,502 nm) | | Content: 99.50% Pb (220,351 nm) | |
| | initial concentration (mg/ml) | measured (mg/ml) | initial concentration (mg/ml) | measured (mg/ml) | initial concentration (mg/ml) | measured (mg/ml) |
| Experiment 1 | 0.696 | 0.116 | 0.397 | 0.138 | 0.597 | 0.004 |
| Experiment 2 | 0.696 | 0.117 | 0.397 | 0.148 | 0.597 | 0.003 |

The measured values found were already converted in accordance with the dilution factor.

It was found that 83% of As was removed/broken down by sporopollenin, between 62% and 65% of Cd was removed/broken down by sporopollenin and 99% of Pb was removed/broken down by sporopollenin.

The invention claimed is:

1. A sporopollenin composition, present as a solution which comprises 0.01% to 12% by weight of sporopollenin, 0.01% to 17% by weight of at least one emulsifier and 71.00% to 99.98% by weight of at least one hydrophilic solvent.

2. The composition according to claim 1, wherein the emulsifier is a hydrolyzable ester compound.

3. The composition according to claim 1, wherein the emulsifier is a hydrophilic non-ionic emulsifier.

4. The composition according to claim 1, wherein the hydrophilic solvent is water and/or a hydrophilic organic solvent.

5. The composition according to claim 1, which further comprises a pharmaceutically acceptable inert auxiliary agent or additive.

6. The composition according to claim 1, in a form selected from the group consisting of an oil, an ointment, a cream, a gel embedded in liposomes, a milk and a solid stick.

7. The composition according to claim 6, wherein sporopollenin is used as a solid.

8. The composition according to claim 1, in a form selected from the group consisting of an oil, a cream and a capsule.

9. The composition according to claim 8, wherein sporopollenin is used as a solid.

10. The composition according to claim 8, wherein the capsule contains sporopollenin as a solid.

11. The composition according to claim 1 comprising 0.1% to 5% by weight, of sporopollenin.

12. The composition according to claim 1 comprising 0.1% to 10% by weight, of at least one emulsifier.

13. The composition according to claim 1 comprising 85% to 99.80% by weight, of at least one hydrophilic solvent.

14. The composition according to claim 4 wherein the hydrophilic organic solvent is an alcohol, optionally containing water, having up to 22 carbon atoms and/or an ester having 2 to 33 carbon atoms.

15. An antimicrobial pharmaceutical composition for treating a microbial disease, which comprises 0.01% to 12% by weight of sporopollenin, 0.01% to 17% by weight of at least one emulsifier, and 71.00% to 99.98% by weight of at least one hydrophilic solvent, together with a pharmaceutically acceptable inert carrier suitable for topical, oral or parenteral administration.

16. A cosmetic composition for treating age-related or sunlight-induced wrinkle formation, which comprises 0.01% to 12% by weight of sporopollenin, 0.01% to 17% by weight of at least one emulsifier, and 71.00% to 99.98% by weight of at least one hydrophilic solvent, together with a cosmetically acceptable inert carrier, suitable for topical administration.

17. A nutritional supplement for vertebrates, which comprises (a) a feed for vertebrates and (b) as a supplement, a sporopollenin composition admixed with the feed and comprising:

0.01% to 12% by weight of sporopollenin, 0.01% to 17% by weight of at least one emulsifier, and 71.00% to 99.98% by weight of at least one hydrophilic solvent.

18. A supplemented beverage, which comprises:

(a) a beverage; and (b) as a supplement, a sporopollenin composition admixed with the beverage and comprising:

0.01% to 12% by weight of sporopollenin, 0.01% to 17% by weight of at least one emulsifier, and 71.00% to 99.98% by weight of at least one hydrophilic solvent.

19. The nutritional supplement defined in claim 17 containing sporopollenin as a solid.

20. The supplemented beverage defined in claim 18 wherein the supplement contains sporopollenin as a solid.

* * * * *